July 29, 1947. R. L. BYRUM Plant Pat. 749
ROSE PLANT
Filed July 23, 1946
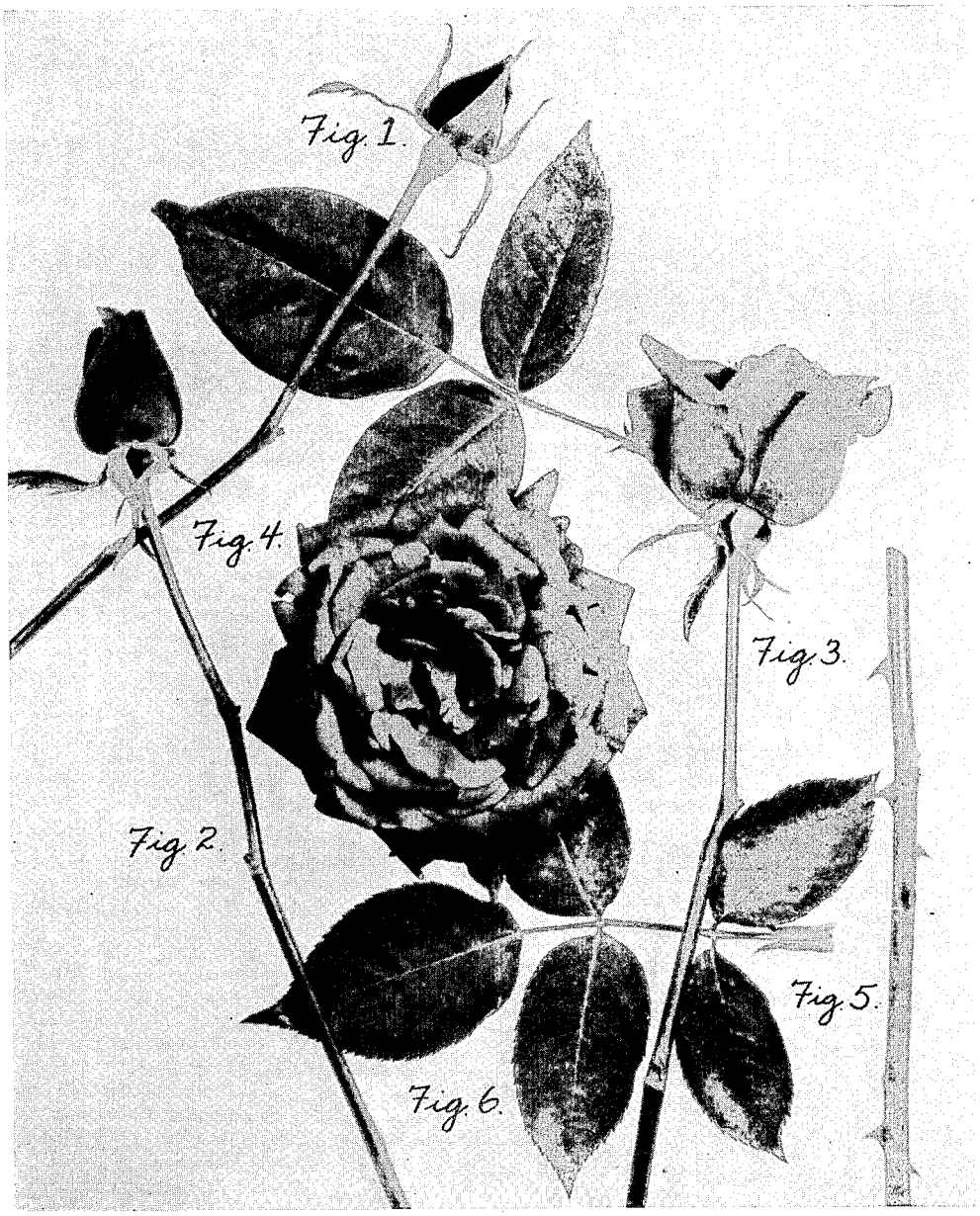
Inventor
R. L. Byrum
By Robbins Robb
attorneys Patented July 29, 1947

Plant Pat. 749

UNITED STATES PATENT OFFICE

749

ROSE PLANT

Roy L. Byrum, Richmond, Ind., assignor to Joseph H. Hill Company, Richmond, Ind., a corporation of Indiana Application July 23, 1946, Serial No. 685,608

1 Claim. (Cl. 47—61)

The present discovery relates to a new and distinct variety of rose plant, originating as a sport of the variety "Spitfire" (Pl. Pat. #617).

This sport variety attracted my attention while growing on a "Spitfire" plant because of its much larger flower in comparison with those of the parent variety. Aside from this dominating large size flower characteristic, this new variety appears to be substantially identical with the "Spitfire" variety when grown under comparable conditions, but I have noted other minor distinguishing characteristics hereinafter more fully presented.

In the drawing:

Fig. 1 is a view showing the bud as calyx breaks;

Fig. 2 is a view of the bud as first petals open;

Fig. 3 shows the bloom at the half-blown stage;

Fig. 4 shows the full-blown flower;

Fig. 5 is a view of a section of a branch disclosing the arrangement and form of the thorns; and Fig. 6 depicts a specimen of the foliage and stipules.

Asexual reproduction of this new variety shows the foregoing characteristics come true to form and are established. It can be successfully propagated by cuttings, grafting and budding. Layering has not yet been tried.

Since the variety nearest to this sport is its parent variety "Spitfire," a general comparison of the characters of the two will best disclose the distinctions.

(*a*) The flowers of the sport are borne singly to a stem which is long and strong, while those of "Spitfire" are borne on normal short stems.

(*b*) In the bud stage, the peduncle is medium long, heavy, reddish green, with few yellow prickles, while in "Spitfire" the peduncle is short, medium heavy, reddish bronze, with few yellow hairs.

(*c*) Before the calyx breaks, it is medium large and in some cases with much cut foliaceous parts, while "Spitfire" is small.

(*d*) As the first petal opens, the size is medium; in "Spitfire," small.

(*e*) The bloom when fully opened is medium large, four to five inches, while in "Spitfire" it is small, two to three inches.

(*f*) The petalage is the same as "Spitfire."

(*g*) Foliage is large, as compared with only medium large in "Spitfire."

(*h*) The rachis is heavy, while in "Spitfire" it is only medium heavy.

(*i*) The canes are heavy; in "Spitfire," only moderately so.

(*j*) The color of the two flowers is identical.

I claim:

A new and distinct variety of hybrid tea rose plant, characterized as to novelty by larger blooms, larger petals, stems, foliage and heavier canes, than found in its parent variety while identical therewith in other respects, substantially as shown and described.

ROY L. BYRUM.